United States Patent
Cottingham et al.

(12)
(10) Patent No.: US 6,194,466 B1
(45) Date of Patent: Feb. 27, 2001

(54) USE OF METFORMIN TO COUNTERACT WEIGHT GAIN ASSOCIATED WITH VALPROATE AND OTHER PSYCHOTROPIC MEDICATIONS

(76) Inventors: Elizabeth Marie Cottingham, 300 Warren Ave., Cincinnati, OH (US) 45219; John Ainslie Morrison, 3740 Clifton Ave., Cincinnati, OH (US) 45220

( * ) Notice: Subject to any disclaimer, the term of this patent is extended or adjusted under 35 U.S.C. 154(b) by 0 days.

(21) Appl. No.: 09/416,330

(22) Filed: Oct. 12, 1999

Related U.S. Application Data

(60) Provisional application No. 60/104,394, filed on Oct. 15, 1998.

(51) Int. Cl.$^7$ .......................... A61K 31/155; A61K 31/19

(52) U.S. Cl. ............................................ 514/635; 514/557

(58) Field of Search ...................... 514/635, 557

(56) References Cited

PUBLICATIONS

Karttunen P. et al. "The pharmacokinetics of metformin: a compairson of the properties of a rapid–release and a sustained–release prepartion"; vol. 21 (1), pp. 31–36, Jan. 1993.*

Jackson, et al. Diabetes 36: 632–640 (1987).
Landin, et al. J. Intern. Med. 229: 181–187 (1991).
Mattson, et al. N. Eng. J. Med. 327: 765–771 (1992).
Verity, et al. Dev. Med. and Child Neurology 37: 97–108 (1993).
Isojarvi, et al. N. Eng. J. Med. 329: 1383–1388 (1993).
Valazquez, et al. Metabolism 43: 647–654 (1994).
Valazquez, et al. Metabolism 46: 454–457 (1997).
Nestler, et al. N. Eng. J. Med. 338: 1876–1880 (1998).
Freeman, et al. Am. J. Psychiatry 155: 12–21 (1998).
Physician's Desk Reference 52$^{nd}$ Ed., 1998, pp. 417–434.

* cited by examiner

*Primary Examiner*—Theodore J. Criares
*Assistant Examiner*—J. Kim
(74) *Attorney, Agent, or Firm*—Frost Brown Todd LLC

(57) ABSTRACT

A method for minimizing the weight gain side effect associated with Valproate treatment is disclosed. In this method, Metformin, a biguanide compound, is concurrently administered to a patient taking the Valproate therapy. A pharmaceutical composition containing the combination of Valproate and Metformin is also disclosed.

10 Claims, No Drawings

USE OF METFORMIN TO COUNTERACT WEIGHT GAIN ASSOCIATED WITH VALPROATE AND OTHER PSYCHOTROPIC MEDICATIONS

This application is based on and claims priority from U.S. provisional application Ser. No. 60/104,394, Cottingham and Morrison, filed Oct. 15, 1998.

TECHNICAL FIELD

The present invention relates to improvements in the treatment of patients for seizure, bipolar disorders and psychoses.

BACKGROUND OF THE INVENTION

Clinical experience and published studies indicate the effectiveness of Valproate (depakote) in the treatment of seizure disorders and bipolar disorders. See, for example, Mattson, et al., Department of Veterans Affairs Epilepsy Cooperative Study No. 264: A Comparison of Valproate with Carbazapine for the Treatment of Complex Partial Seizures and Secondarily Generalized Tonic-Chronic Seizures In Adults. N. Eng. J. Med., 327: 765–771 (1992); Freeman, et al., Mood Stabilizer Combinations: A Review of Safety and Efficacy. Am. J. Psychiatry, 155: 12–21 (1998); and Verity, et al., A Multi-Center Comparative Trial Of Sodium Valproate And Carbamazepine In Pediatric Epilepsy. Developmental Medicine And Child Neurology, 37: 97–108 (1993). Use of Valproate, however, is also associated with side effects in as many as 50% of the patients taking it; these side effects include marked weight gain. Isojarvi et al., Polycystic Ovaries And Hyperandrogenism In Women Taking Valproate For Epilepsy, N. Eng. J. Med., 329: 1383–1388 (1993). Although not all patients experience this weight gain side effect, in those that do, the weight gain can be considerable, as much as 40–50 pounds. This side effect presents a number of patient issues, both medical and psychological, for the treating physician to consider. Such a marked weight gain can place a significant burden on the heart and circulatory system of the patient. In addition, particularly in-patients suffering from depression, such weight gain can hurt self-image and adversely impact the depressed state. Finally, and perhaps most importantly, such side effects can reduce patient compliance with the therapy regimen, thereby resulting in ineffective treatment for the primary disorder. Identification of a means to counteract these side effects partially or completely is, therefore, important. There is at present no way to prevent or treat obesity associated with the use of Valproate, except through behavioral changes such as increased physical activity or decreased caloric intake.

Metformin is a biguanide drug which is known to improve insulin action at the cellular level, but not affect insulin secretion. Metformin is used to treat patients with non-insulin dependent diabetes and has recently been used to treat women with polycystic ovary syndrome, a syndrome characterized by hirsutism, hyperandrogenism, and polycystic ovaries. It has not, however, been suggested for use in controlling the weight gain caused by Valproate or other psychotropic actives. See, for example, Valazquez, et al, Metformin Therapy Is Associated With A Decrease In Plasma Plasminogen Activator Inhibitor-1, Lipoprotein (a) and Immunoreactive Insulin Levels In-Patients With Polycystic Ovary Syndrome. Metabolism, 46: 454–457 (1997); Valazquez, et al, Metformin Therapy In Polycystic Ovary Syndrome Reduces Hyperinsulinemia, Insulin Resistance, Hyperandrogenism, And Systolic Blood Pressure, While Facilitating Normal Menses And Pregnancy. Metabolism, 43: 647–654 (1994); Jackson, et al., Mechanism of Metformin Action In Non-Insulin Dependent Diabetes. Diabetes; 36: 632–640 (1987); Landin, et al., Treating Insulin Resistance in Hypertension With Metformin Reduces Both Blood Pressure And Metabolic Risk Factors. J. Intern. Med.; 229: 181–187 (1991); and Nestler, et al., Effects of Metformin on Spontaneous and Clomiphene-Induced Ovulation in the Polycystic Ovary Syndrome. N. Engl. J. Med. 338: 1876–1880 (1998).

SUMMARY OF THE INVENTION

The present invention relates to a method for minimizing weight gain in a patient taking a psychotropic active selected from the group consisting of Valproate, Risperdal, Lithobid, Zyprexa and Seroquel (most preferably Valproate), comprising the administration to said patient of a safe and effective amount of Metformin or a similar compound.

The present invention also encompasses a combination drug composition which comprises a safe and effective amount of a psychotropic active select from the group consisting of Valproate, Risperdal, Lithobid, Zyprexa and Seroquel (most preferably Valproate), together with a safe and effective amount of Metformin or a similar compound

DETAILED DESCRIPTION OF THE INVENTION

The present invention relates to a method for minimizing weight gain in a patient taking Valproate or other selected psychotropic medications.

Valproate sodium is the sodium salt of valproic acid, designated as sodium-2-propylpentanoate. Valproate sodium (Divalproex sodium; Depakote) has the structure shown below:

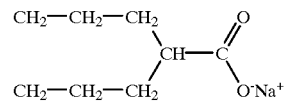

It has a molecular weight of 166.2 and occurs as an essentially white and odorless, crystalline, deliquescent powder. Valproate sodium is typically prescribed for the treatment of epilepsy and other seizure disorders, as well as bipolar disorder. Valproate is typically available for administration orally in tablets or capsules (Depakote, manufactured and sold by Abbott Laboratories), and by intravenous injection (Depacon, manufactured and sold by Abbott Laboratories). Valproate is typically administered to a patient in need of such treatment at a dosage of about 20 mg/kg. Valproic acid (Depakene) also has associated weight gain side effects. As used herein, "Valproate" is intended to include valproic acid and its pharmaceutically-acceptable salts.

Other psychotropic actives that have an associated weight gain side effect may also be used in the present invention (i.e., they may be administered in combination with Metformin to reduce the weight gain side effect). Examples of such psychotropic actives include Risperdal (Risperidone), a medication that is prescribed for patients with psychotic disorders, tic disorders and bipolar disorder (commercially available from Janssen Pharmaceuticals); Lithobid (Lithium), a medication that is prescribed for patients with bipolar disorder (commercially available from Solvay Pharmaceuticals); Zyprexa (Olanzapine), a medication that is prescribed for patients with psychotic disorders, tic disorders and bipolar disorder (commercially available from Eli-Lilly & Company); and Seroquel (quetiapine), an antipsychotic medication that is prescribed for patients with psychotic disorders, tic disorders and bipolar disorder (commercially available from Zeneca Pharmaceuticals). All of these actives exhibit a significant weight gain side effect with certain patients, and this side effect can be minimized using the concurrent Metformin therapy described herein.

Metformin hydrochloride is a biguanide compound that is generally prepared as an oral anti-hyperglycemic drug used in the management of non-insulin-dependent diabetes mellitus. It is typically prepared in the form of tablets and is commercially available as Glucophage from the Bristol-Myers Squibb Company. Metformin hydrochloride (N,N-dimethylimidocarbonimidic diamide hydrochloride) has the structural formula shown below:

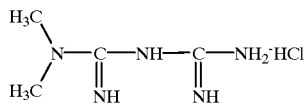

In addition to Metformin hydrochloride, other pharmaceutically-acceptable salts of Metformin may be used. Metformin hydrochloride is a white to off-white crystalline compound with a molecular formula of $C_4H_{11}N_5 \cdot HCl$, and a molecular weight of 165.63. Metformin hydrochloride is freely soluble in water and is practically insoluble in acetone, ether or chloroform. The $pK_a$ of Metformin is 12.4. The pH of a 1% aqueous solution of Metformin hydrochloride is 6.68. Glucophage tablets contain 500 mg or 850 mg of Metformin hydrochloride. In addition, each tablet contains the following inactive ingredients: povidone, magnesium stearate and hydroxypropyl methylcellulose coating.

The Metformin dosage forms used in the present invention optionally may be formulated for controlled release, sustained release or response release (i.e., the tablet is ingested and the active is released in response to the intake of food by the patient).

In practicing the method of treatment of the present invention, Metformin (or another pharmaceutically-acceptable salt of N,N-dimethylimidocarbonimidic diamide) is administered to a patient on Valproate therapy (or therapy with another of the psychotropic actives described above). The Valproate or other psychotropic actives will be administered using their conventional routes of administration and their conventional dosage levels. Metformin may be administered to the patient in any way known in the art, although oral administration will generally be most convenient. Metformin is administered in an amount that is safe and effective for minimizing the weight gain associated with Valproate therapy, preferably at a level of from about 1500 to about 2500 mg per day. It is typically administered with meals at a dosage of 500 mg tid.

The present invention also encompasses a combination drug that includes both Valproate or the other psychotropic actives described above, together with Metformin or other biguanide compounds (including other pharmaceutically-acceptable salts of N,N-dimethylimidocarbonimidic diamide). This combination of drugs is typically formulated as a tablet or capsule for oral administration, although other routes of administration, such as intravenous injection can also be used. A tablet or capsule for oral administration of the present invention would typically include from about 250 mg to about 500 mg of Valproate, and from about 250 mg to about 850 mg of Metformin. Conventional formulational aides, such as fillers, coatings, preservatives, disintegration aides, colorings and flavorings, can also be included at their conventional art-established levels. When the composition contains other actives, in place of Valproate, their levels per dosage typically would be as follows: Risperdal: from about 1 mg to about 4 mg; Lithobid; from about 300 mg to about 450 mg; Zyprexa: from about 2.5 mg to about 10 mg; and Seroquel: from about 25 mg to about 200 mg.

By "pharmaceutically-acceptable", as used herein, is meant that the drug-active compounds and other ingredients used in the present methods and compositions, are suitable for use in contact with the tissues of humans without undue toxicity, irritation, allergic response, and the like, commensurate with a reasonable benefit/risk ratio.

What is claimed is:

1. A method for minimizing weight gain in a patient taking a psychotropic active compound selected from the group consisting of Valproate, Risperdal, Lithobid, Zyprexa, and Seroquel, comprising the administration to said patient of a safe and effective amount of a weight control active compound comprising a pharmaceutically-acceptable salt of N,N-dimethylimidocarbonimidic diamide.

2. The method according to claim 1 wherein the weight control active is the hydrochloride salt.

3. The method according to claim 2 wherein the psychotropic active compound is Valproate.

4. The method according to claim 3 wherein the weight control active compound is administered orally.

5. The method according to claim 4 wherein the weight control active compound is administered in an amount of from about 1500 mg to about 2500 mg per day.

6. A pharmaceutical composition comprising a safe and effective amount of a psychotropic active compound selected from the group consisting of Valproate, Risperdal, Lithobid, Zyprexa and Seroquel, together with a weight control active compound comprising a pharmaceutically-acceptable salt of N,N-dimethylimidocarbonimidic diamide in an amount safe and effective for minimizing weight gain caused by said psychotropic active in the patient taking said psychotropic active.

7. The composition according to claim 6 wherein the weight control active compound is the hydrochloride salt.

8. The composition according to claim 7 wherein the psychotropic active compound is Valproate.

9. The composition according to claim 8 which is formulated for oral administration.

10. The composition according to claim 9 which contains from about 250 mg to about 500 mg Valproate, and from about 250 mg to about 500 mg of the weight control active compound.

* * * * *